(12) United States Patent
Cheng et al.

(10) Patent No.: US 6,770,760 B2
(45) Date of Patent: Aug. 3, 2004

(54) NUCLEIC ACID BULGE-DETECTING AGENT

(75) Inventors: Chien-Chung Cheng, Taipei (TW); Wen Jwu Wang, Taipei (TW)

(73) Assignee: Academia Sinica, Taipei (TW)

( * ) Notice: Subject to any disclaimer, the term of this patent is extended or adjusted under 35 U.S.C. 154(b) by 390 days.

(21) Appl. No.: 10/039,069

(22) Filed: Jan. 2, 2002

(65) Prior Publication Data

US 2002/0095029 A1 Jul. 18, 2002

Related U.S. Application Data

(62) Division of application No. 09/302,334, filed on Apr. 30, 1999, now Pat. No. 6,348,588.

(51) Int. Cl.[7] .......................... C07D 221/18; C07H 21/00
(52) U.S. Cl. .......................................... 546/61; 536/25.3
(58) Field of Search ............................ 536/25.3; 546/61

(56) References Cited

U.S. PATENT DOCUMENTS 6,348,588 B1 * 2/2002 Cheng et al. ............... 536/25.3

OTHER PUBLICATIONS

Chang et al., "Metal Ion Dependent Binding and Nuclease Activity of Hexaazacyclophane", Journal of the Chinese Chemical Society 43:73–75, 1996.
Kappen et al., "Bulge–Specific Cleavage in Transactivation Response Region RNA and Its DNA Analogue by Neocarzinostatin Chromophore", Biochemistry 34:5997–6002, 1995.
Kappen et al., "Characterization of a Covalent Monoadduct of Neocarzinostatin Chromophore at a DNA Bulge", Biochemistry 36:14861–14867, 1997.
Kappen et al., "DNA Conformation–Induced Activation of an Enediyne for Site–Specific Cleavage", Science 261:1319–1321, 1993.
Kappen et al., "Site–Specific Cleavage at a DNA Bulge by Neocarzinostatin Chromophore Via a Novel Mechanism", Biochemistry 32:13138–13145, 1993.
Kunkel, "Misalignment–mediated DNA Synthesis Errors", Biochemistry 29:8003–8011, 1990.
Lilley, "Kinking of DNA and RNA by Base Bulges", Proc. Natl. Acad. Sci. USA 92:7140–7142, 1995.
Malkov et al., "Photocross–linking of the $Nh_2$–terminal Region of Taq MutS Protein to the Major Groove of a Heteroduplex DNA", Journal of Biological Chemistry 272:23811–23817, 1997.
Rice et al., "DNA Bending by the Bulge Defect", Biochemistry 28:4512–4516, 1989.
Rommens et al., "Rapid Nonradioactive Detection of the Major Cystic Fibrosis Mutation", Am. J. Hum. Genet. 46:396–397, 1990.
Stassinopoulos et al., "Probing the Structure of Long Single–Stranded DNA Fragments with Neocarzinostatin Chromophore. Extension . . . ", Biochemistry 34:15359–15374, 1995.
Stassinopoulos et al., "Solution Structure of a Two–Base DNA Bulge Complexed with an Enediyne Cleaving Analog", Science 272:1943–1946, 1996.
Streisinger et al., "Frameshift Mutations and the Genetic Code", Cold Spring Harb Symp Quant Biol. 31:77–84 1966.

(List continued on next page.)

*Primary Examiner*—Ardin H. Marschel
(74) *Attorney, Agent, or Firm*—Fish & Richardson P.C.

(57) ABSTRACT

This invention relates to a metal complex of formula (I). The metal complex is capable of cleaving a bulge-containing nucleic acid at the bulge site with high specificity.

16 Claims, 1 Drawing Sheet

OTHER PUBLICATIONS

Triggs–Raine et al., "Diagnostic Heteroduplexes: Simple Detection of Carriers of a 4–bp Insertion Mutation in Tay–Sachs Disease", Am. J. Hum. Genet. 46:183–184, 1990.

Turner, "Bulges in Nucleic Acids", Current Opinion in Structural Biology 2:334–337, 1992.

Wang et al., "Effects of Bulge Composition and Flanking Sequence on the Kinking of DNA by Bulged Bases", Biochemistry 30:1358–1363, 1991.

Wang et al., "RecA Binding to Bulge– and Mismatch–containing DNAs", The Jounal of Biological Chemistry 268:17571–7577, 1993.

Williams et al., Selective Strand Scission by Intercalating Drugs at DNA Bulges , Biochemistry 27:3004–3011 1988.

Yang et al., "Specific Binding of the Biradical Analog of Neocarzinostatin Chromophore to Bulged DNA: Implications for Thiol–Independent Cleavage", Biochemistry 34:2267–2275, 1995.

* cited by examiner

NUCLEIC ACID BULGE-DETECTING AGENT

This application is a divisional application of U.S. Ser. No. 09/302,334 filed Apr. 30, 1999, now U.S. Pat. No. 6,348,588.

BACKGROUND OF THE INVENTION

Nucleic acid bulges refer to regions of unpaired bases in a double-stranded nucleic acid molecule. These bulges have been known to take part in many important biological processes.

For example, ENA bulges form crucial motifs for specific nucleic acid-protein recognition and binding. It has been known that the human immunodeficiency virus transactivator protein Tat binds to a three-pyrimidine bulge in the response element TAR. See, e.g., Weeks et al., *Science* 249, 1281-1285 (1990). Nucleic acid bulges also produce frameshift mutations which can change the product of the protein translation and result in various disorders. According to one report, Myerowitz et al., *J. Biol. Chem.* 263, 18587-18589 (1988), approximately 70% of Ashkenazi Tay-Sachs disease is caused by a four-base pair insertion mutation in the HEX A gene encoding the α-subunit of hexosaminidase A. Another disease, cystic fibrosis, is also caused by frameshift mutation. A three-base pair deletion (AF508) is commonly found among cystic fibrosis patients. Rommens et al., *Am. J. Hum. Genet.* 46, 395-396 (1990).

Comparative gel electrophoresis assay has been used to detect the presence of bulges in nucleic acids. This assay differentiates nucleic acids with and without bulges by their different mobility in gel. However, it can only provide information as to whether a nucleic acid contains a bulge. Thus, there exists a need for a detection method which can provide additional information, e.g., the location of a bulge in a nucleic acid.

SUMMARY OF THE INVENTION

One aspect of this invention relates to a metal complex of formula (I):

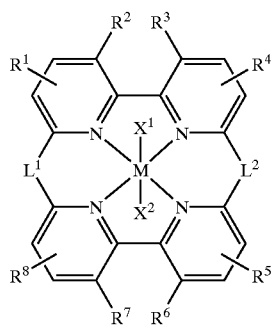

(I)

Each of $R^1$, $R^2$, $R^3$, $R^4$, $R^5$, $R^6$, $R^7$ and $R^8$, independently, is hydrogen, alkyl, alkoxy, hydroxyl, hydroxylalkyl, halo, haloalkyl, amino, aminoalkyl, alkylcarbonylamino, alkylaminocarbonyl, alkylcarbonyl, alkylcarbonylalkyl, alkoxycarbonyl, alkylcarbonyloxy, cycloalkyl, heterocycloalkyl, aryl, aralkyl, heteroaryl, or heteroaralkyl. Each of $R^2$ and $R^3$, and $R^6$ and $R^7$, independently, optionally join together to form a cyclic moiety which is fused with the two pyridyl rings to which $R^2$ and $R^3$, or $R^6$ and $R^7$ are bonded. The cyclic moiety, if present, is optionally substituted with alkyl, alkoxy, hydroxyl, hydroxylalkyl, halo, haloalkyl, amino, aminoalkyl, alkylcarbonylamino, alkylaminocarbonyl, alkylcarbonyl, alkylcarbonylalkyl, alkoxycarbonyl, alkylcarbonyloxy, cycloalkyl, heterocycloalkyl, aryl, aralkyl, heteroaryl, or heteroaralkyl. Each of $L^1$ and $L^2$, independently, is —C($R^a$)($R^b$)—, —O—, —S—, or —N($R^c$)— and each of $R^a$, $R^b$, and $R^c$, independently, is hydrogen, alkyl, cycloalkyl, heterocycloalkyl, aryl, heteroaryl, aralkyl, or heteroaralkyl. M is a Co, Ni, Ru, Rh, Mn, Os, Ag, Cr, Zn, Cd, Hg, Re, Ir, Pt, or Pd ion, and the oxidation state of M is 0, 1, 2, 3, or 4. Each of $X^1$ and $X^2$, independently, is a labile ligand.

Examples of a metal complex of formula (I) include cobalt(II)(hexaazacyclophane)(trifluoroacetate)$_2$, cobalt (II) (hexaazacyclophane) ($H_2O$) (trifluoroacetate) ruthenium(II) (hexaazacyclophane) (trifluoroacetate)$_2$, and manganese(II) (hexaazacyclophane)(trifluoroacetate)$_2$.

Another aspect of this invention relates to a method of specifically cleaving a nucleic acid bulge. The method comprising contacting the bulge with a metal complex of formula (I), supra, where M is a Fe, Co, Ni, Ru, Rh, Mn, Os, Ag, Cr, Zn, Cd, Hg, Re, Ir, Pt, or Pd ion. In one embodiment, the method is performed in the presence of an oxidant, e.g., hydrogen peroxide, or in a medium having a pH values which ranges from 4-9.

In this disclosure, a nucleic acid bulge is a region in a double-stranded nucleic acid molecule (DNA or RNA), the region having at least one unpaired nucleotide and being flanked by two paired nucleotides. The nucleic acid bulge can contain 1-5 unpaired nucleotides (e.g., 1-3). Using nucleic acid substrate A in FIG. 1 as an example, the nucleic acid bulge present therein contains three unpaired nucleotides, i.e., $T_6$, $C_7$, and $T_8$. This three-base bulge is flanked by two paired nucleotides, i.e., $A_5$-$T_{23}$ and $G_9$-$C_{22}$. In contrast, the $C_{13}$-$A_{18}$ hairpin loop, which is also present in substrate A, is not a bulge as the unpaired nucleotides are only connected to one paired nucleotide, i.e., $C_{12}$-$G_{19}$. A nucleic acid bulge can also contain two nucleotides. See the bulge present in substrate D which is formed of two unpaired nucleotides, i.e., $C_6$ and $T_7$.

A salt of a metal complex of formula (I) is also within the scope of this invention. Note that a metal complex of formula (I) can be positively charged. A salt of such a metal complex can be formed with an anionic counterion. Examples of counterions include fluoride, chloride, bromide, iodide, sulfate, sulfite, phosphate, acetate, oxalate, and succinate.

As described above, each of $R^2$ and $R^3$, and $R^6$ and $R^7$, independently, can join together to form a cyclic moiety. The cyclic moiety can contain 5 or 6 ring members and can be cycloalkyl, heterocycloalkyl, aryl, or heteroaryl. For example, when the cyclic moiety formed by joining $R^2$ and $R^3$ is a benzene, it fuses with the two pyridine rings co which $R^2$ and $R^3$ are bonded, and the benzene ring and the two pyridine rings together form phenanthroline.

As used herein, alkyl is a straight or branched hydrocarbon chain containing 1 to 6 carbon atoms. Examples of alkyl include, but are not limited to, methyl, ethyl, propyl, isopropyl, butyl, isobutyl, tert-butyl, and hexyl.

By "cycloalkyl" is meant a cyclic alkyl group containing 3 to 8 carbon atoms. Some examples of cycloalkyl are cyclopropyl, cyclopentyl, cyclohexyl, cycloheptyl, adamantyl, and norbornyl. Heterocycloalkyl is a cycloalkyl group containing 1-3 heteroatoms such as nitrogen, oxygen, or sulfur. Examples of heterocycloalkyl include piperidine, piperazine, tetrahydropyran, tetrahydrofuran, and morpholine.

In this disclosure, aryl is an aromatic group containing 6-12 ring atoms and can contain fused rings, which may be saturated, unsaturated, or aromatic. Examples of an aryl group include phenyl and naphthyl. Heteroaryl is aryl containing 1-3 heteroatoms such as nitrogen, oxygen, or sulfur. Examples of heteroaryl include pyridyl, furanyl, pyrrolyl, thienyl, thiazolyl, oxazolyl, imidazolyl, indolyl, benzofuranyl, and benzothiazolyl.

Note that an amino group can be unsubstituted, mono-substituted, or di-substituted. It can be substituted with groups such as alkyl, cycloalkyl, heterocycloalkyl, aryl, or heteroaryl. Halo refers to fluoro, chloro, bromo, or iodo.

A labile ligand (i.e., $X^1$ or $X^2$) refers to a group which coordinates with less affinity to the metal ion (i.e., M) of a complex of formula (I) relative to the four pyridyl nitrogen atoms. Such ligand can therefore undergo rapid equilibrium with other labile ligands. Examples of a labile ligand include $H_2O$, Cl, trifluoroacetate, or pyridine.

A metal complex of formula (I) possesses unexpectedly high specificity toward nucleic acid containing a bulge structure. As described above, a nucleic acid with such a structure is associated with various disorders. A metal complex of formula (I) can therefore be used in a diagnostic kit for detecting nucleic acid bulge-associated disorders.

Other features or advantages of the present invention will be apparent from the following detailed description of several embodiments, and also from the appending claims.

DETAILED DESCRIPTION OF THE INVENTION

Figure 1:
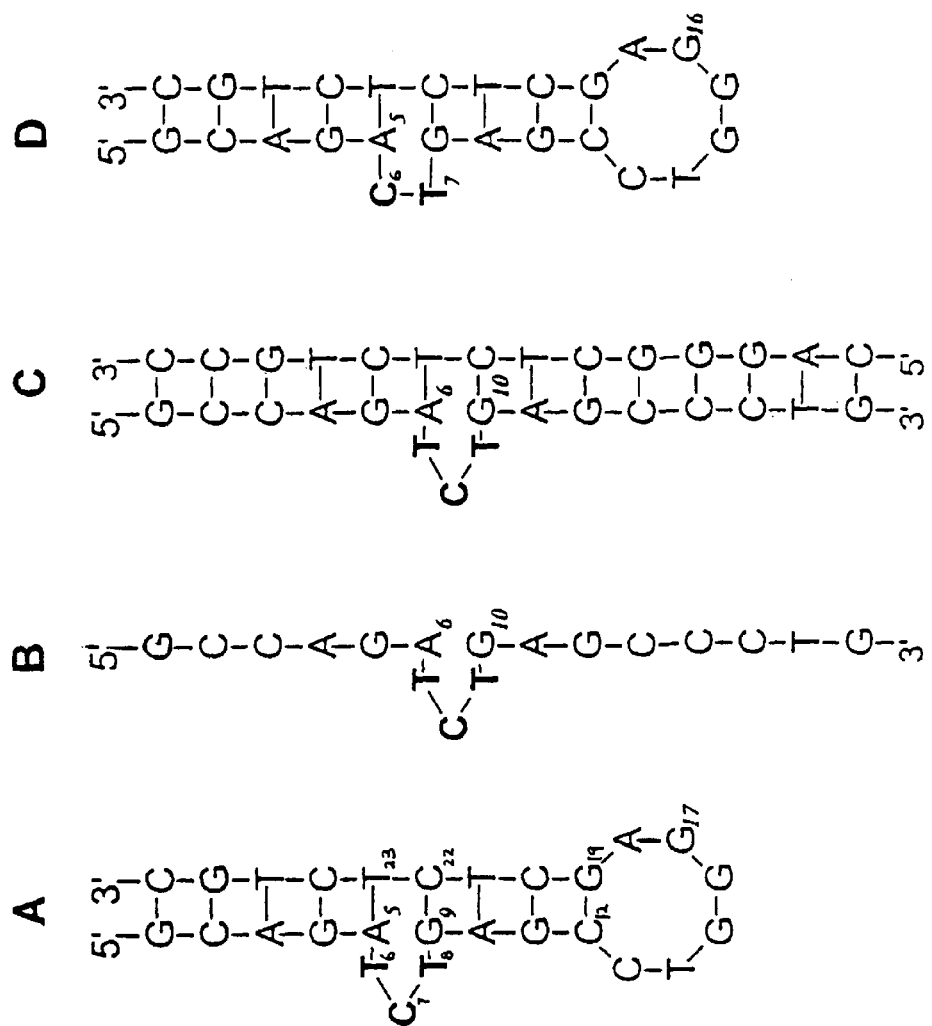
FIG. 1 depicts the sequence of each of nucleic acid substrates A-D used in Examples 1-3 below.

The invention features metal complexes of formula (I) which specifically target bulge structures in a nucleic acid molecule Metal complexes of formula (I) can therefore be used in detecting nucleic acid bulges for diagnostic purposes. A method of specifically cleaving a nucleic acid bulge using a metal complex of formula (I) is also within the scope of this invention.

A number of methods can be used to prepare the metal complexes of formula (I). For example, when each of $L^1$ and $L^2$ is —N($R^c$)— where $R^c$ is H, the hexaazacyclophane car be formed by reacting 2,9-diamino-1,10-phenanthroline with 2,9-dichloro-1,10-phenanthroline the presence of nickel (II) ion, which can then be removed by using trifluoroacetic acid. See, e.g., Chang et al., *J. Chin. Chem.* 43, 73-75 (1996).

Alternatively the method described above can be modified as shown in steps i, ii, and iii of the following scheme:

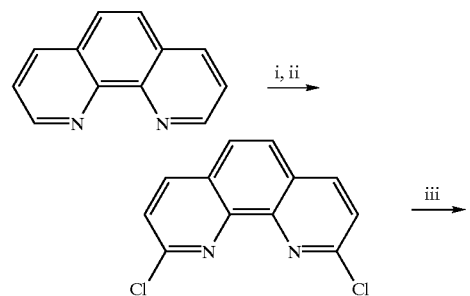

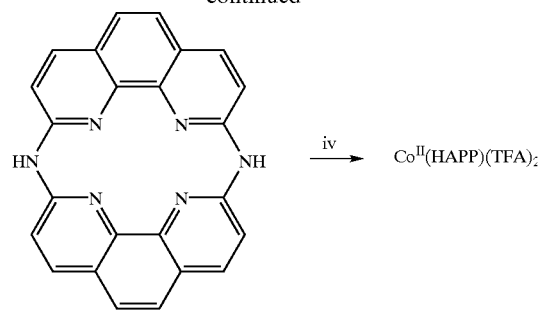

Reagents and conditions i, $CH_3L$ $K_3Fe(CN)_6$/NaOH(aq); ii, $PCl_5$, $POCl_3$, 75% iii, $NH_{3(g)}$, 200° C. 80%, iv, $Co(OAc)_2$ in $TFA/MeOH/CH_2Cl_2$, reflux, 64%.

As shown in step iv above, the desired metal ion, e.g., cobalt(II), can be coordinated to the hexaazacyclophane ligand at the same time as two axial ligands, e.g., trifluoroacetate, are coordinated to the metal ion. Substituents on the aromatic rings can be introduced either before or after the preparation of the ligand by methods familiar to one of ordinary skill in the art, e.g., electrophilic aromatic substitution.

Complexes of formula (I) where each of $L^1$ and $L^2$ is —S— can be prepared in an analogous way by reacting starting materials such as 2,9-dichloro-1,10-phenanthroline in $H_2S$ gas instead of ammonia gas (see step iii of the above scheme). On the other hand, a complex of formula (I) where each of $L^1$ and $L^2$ is —O— or —C($R^a$) ($R^b$)— can be prepared by reacting compounds such as 1,10-phenanthroline-2,9-diboronic acid and 2,9-dihydroxy-1,10-phenanthroline in the presence of a palladium catalyst such as $Pd(PPh_3)_4$.

Note that the metal ion of each of the complexes of formula (I) adopts an octahedral coordination. For example, the X-ray crystal structure of cobalt(II)(hexaazacyclophane)(trifluoroacetate)$_2$, i.e., $Co^{II}$ (HAPP)(TFA)$_2$, reveals that the complex contains two labile axial TFA ligands, and two linked 1,10-phenanthroline moieties where all four pyridyl nitrogen atoms are locating on the same coordination plane. The average Co-N distance is approximately 1.86 ÅEPR spectrum of the $Co^{II}$ complex gave a $g_{av}$ value at 2.005–2.331 in methanol, indicating the presence of an octahedral $Co^{II}$ complex. When one equivalent of pyridine was added, it rapidly displaced one of the axial TEA ligands under ambient conditions, as monitored by EPR spectroscopy, suggesting that the TFA ligands are labile. The TFA ligands can also be readily substituted by water upon dissolution of the complex in aqueous buffer.

Due to the steric hindrance brought about by its octahedral structure, a metal complex of formula (I) does not intercalate in between bases of a nucleic acid molecule. Using $Co^{II}$(HAPP) (TFA)$_2$ as an example, a topoisomerase I assay conducted in the absence of $H_2O_2$ and under non-cleavage conditions (vide infra) showed no sign of DNA unwinding resulted from DNA intercalation. Further, under the same non-cleavage conditions, a native gel mobility shift assay conducted using the $Co^{II}$ complex also showed no indication of the presence of high-molecular-weight bands attributable to the presence of a DNA-$Co^{II}$ complex adduct in polyacrylamide gel electrophoresis. In addition, the melting temperature of calf thymus DNA (60 $\mu$M per nucleotide) incubated with the $Co^{II}$ complex (8 $\mu$M) only changed by 0.5-1.0° C. In contrast, incubation of DNA with ethidium bromide, a known DNA intercalator, resulted in a DNA-ethidium bromide adduct with a melting temperature differing by 12-13° C. from the control under identical reaction conditions. Moreover, the DNA-binding constant of the $Co^{II}$ complex, as determined by spectral titration at 399 nm with calf thymus DNA was found to be 10-fold less when compared to another known DNA-intercalator, $Cu^{II}$ $(HAPP)^{+2}$, which adopts a planar structure. Because of its non-intercalating nature, a metal complex of formula (I) can unambiguously detect the location of a bulge in a nucleic acid.

In the presence of $H_2O_2$ (0.005%-0.05%), a metal complex of formula (I) cleaves a nucleic acid molecule containing a bulge catalytically. Although the metal complex can still effect nucleic acid cleavage in the absence of $H_2O_2$, a longer reaction time (about 8-10 times longer) and a higher concentration of the metal complex (about 10-fold higher) are required to produce the same amount of cleavage. When $H_2O_2$ is replaced by magnesium monoperoxyphthalic acid or oxone, no significant nucleic acid cleavage was observed under the same reaction conditions and time. Further, the amount of nucleic acid cleavage was reduced by half when a hydroxyl radical scavenger was added. See Example 1 below. This indicates that hydroxyl radicals are responsible for the nucleic acid cleavage.

Moreover, the metal complex targets nucleic acid with high specificity. Not only does the complex cleave specifically at the bulge structure, the size of such a structure also controls the specificity of the cleavage reaction. It was unexpectedly found that in treating a double-stranded DNA substrate containing a three-base bulge and a six-base hairpin loop with $Co^{II}(HAPP)$ $(TFA)_2$, cleavage occurred specifically at the bulge, and only weakly at the loop. See Example 1 below. As hydroxyl radicals are diffusible and generally lack specificity towards a particular nucleotide or a group of nucleotides, the high specificity must have resulted from a specific recognition between the metal complex and the bulge structure. Indeed, when the just-described nucleic acid was denatured, no specific cleavage was observed at the sequence corresponding to the bulge. See Example 2 below.

Without further elaboration, it is believed that one of ordinary skill in the art can, based on the description herein, utilized parts or the whole procedure to its full extent. The following examples are, therefore, to be construed as merely illustrative, and not limitative of the remainder of the disclosure in any way whatsoever. All publications mentioned above are incorporated by reference in their entirety.

EXAMPLE 1

λ-Phage FC-174 DNA was purchased from Life Technologies (Gibco BRL). No further purification was needed prior to use. The synthetic DNA substrate employed herein was a 27-mer DNA, 5'-GCACATCTGAGCCTGGGA GCTCTCTGC-3' (SEQ ID No. 1) which was purchased from Perkin Elmer Inc. (see nucleic acid substrate A in FIG. 1), and was purified by gel purification in a 20% denaturing polyacrylamide gel (7 M urea). The DNA bands were visualized with an UV lamp ($\lambda_{max}$=254 nm) by placing the gel on a TLC F254 plate (20×20 cm, Merck). After a successive process of excising the desired visible bands, extracting the DNA from gel, and precipitating it by EtOH, a pure DNA was obtained. The DNA concentration was determined using the extinction coefficient ($\lambda_{max}$=260 nm) or molecular weight method (1 OD=about 33 mg and the average molecular weight of one nucleotide=330 daltons).

The 5'-$^{32}$P-end labeled DNA substrate was prepared by using T4 polynucleotide kinase (New England Biolabs) and deoxyadenosine-5'-[γ-$^{32}$P]-triphosphate (Amersham). The excess free γ-$^{32}$P-ATP was removed by filtration with Centricon-10 (Amicon) using ultracentrifuge (6,000 rpm, Beckman GS-15R equipped with rotor F0850) at 4° C. for 80 minutes, followed by an additional centrifuge with Milli-Q water (1 mL) for 60 minutes. A further dilution to proper radiation intensity with deionized water was performed prior to use in assays described below.

Using the 5'-$^{32}$P-end labeled DNA substrate, a modified Maxam-Gilbert G Lane was prepared by cooling a 20 μL solution containing about 10 nCi $^{32}$P-labeled substrate in deionized $H_2O$ to 0-4° C. prior to the addition of dimethyl sulfate. The solution containing the labeled DNA was then vortexed (<1 sec), and 2-mercaptoethanol (10 μL) was immediatelyadded to the solution. The solution was vortexed for an additional 30 seconds. Afteradding to sonicated calf thymus DNA (5 mg) and 3.0 M sodium acetate (pH 7.0, 15 μL) to the solution, the labeled DNA was precipitated with 95% EtOH and centrifuged to obtain a pellet which was then treated with piperidine as described above prior to use as control in a DNA cleavage assay.

In the DNA cleavage assay, a 20 μL solution containing a final concentration of about 8 nCi of 5'-γ-$^{32}$P-labeled substrate (4-5 μM) and unlabeled DNA (4 mM) in 10 mM sodium phosphate buffer (pH 6.96) were combined with $Co^{II}(HAPP)$ $(TFA)_2$ (0.6 μM) and $H_2O_2$ (0.005-0.05%) at 25° C. for 5 minutes. The reaction was quenched by adding sonicated calf thymus DNA (4 mg), 3 M sodium acetate (5 μL, pH 4.5), and 95% EtOH (700 μL), and then stored at −78° C. for 20 minutes, centrifuged (12,000 rpm) at 4° C. for 20 minutes, and finally lyophilized to dryness to form a pellet. The reaction mixture was then subjected to a piperidine treatment by adding 0.7 M piperidine aqueous solution (60 μL) and heating at 90° C. for 30 minutes. After the reaction mixture was lyophilized, washed with deionized $H_2O$, and lyophilized again to dryness, it was resuspended in a gel-loading buffer (5 μL) containing 0.25% bromophenol blue, 0.25% xylene cyanol FF, and 7 M urea. The DNA fragment was analyzed by 20% denaturing polyacrylamide gel (7 M urea) and then visualized using Kodak BioMax MR-1 films with intensifying screens. The optical density of DNA fragments was quantified using image programs from NIH image (free shareware) and UVP Inc. (GelBase/ GelBlotTMPro) equipped with an Vista S-12 scanner (UMAX).

The DNA substrate employed in this example contains a three-base bulge and a six-base hairpin loop (see nucleic acid substrate A in FIG. 1). This DNA sequence was designed based on the RNA hairpin from the trans-activation response element (TAR-RNA). After piperidinetreatment, the strand scission was unexpectedly found to occur specifically at the bulge ($T_6$, $C_7$, and $T_8$) and only very weakly at the hairpin loop ($C_{13}$-$A_{18}$). Note that both the bulge and the loop contain the same 5'-CTG-3' sequence. Minor cleavage was also found at the sites near the flanking junctions of these nucleotides. Further, no significant oxidative cleavage was observed at the 5'-GGG-3' region in the DNA hairpin loop which have been reported to be susceptible to oxidative cleavage due to its low reduction potential. When Pt(terpy) $(HET)^+$ (HET=2-hydroxyethylenethiol), a known DNA intercalator which targets DNA bulges, was added to the reaction, competitive inhibition was observed and the amount of cleavage at the bulge was found to reduce remarkably.

In the absence of $H_2O_2$, the reaction required a higher concentration of the $Co^{II}$ complex (>50 μM) as well as a longer reaction time (>40 minutes) to afford the same amount of DNA cleavage at the bulge. Moreover, when magnesium monoperoxyphthalic acid (MMPP) and oxone $(KHSO_5)$ were used instead of $H_2O_2$, no significant DNA cleavage was observed. Since the addition of superoxide dismutase and $D_2O$ into the reaction medium did not reduce the concentration of circular DNA (Form II) formed in the DNA cleavage products mediated by this $Co^{II}$ complex, superoxide and singlet oxygen species are not involved in this process. Further, when mannitol, a hydroxyl radical scavenger, was added into the DNA cleavage assay medium, the amount of circular DNA (Form II) was found to be reduced by half.

The results described above showed that (1) $Co^{II}$ (HAPP) $(TFA)_2$ specifically cleaves DNA bulge, and (2) the cleavage reaction is effected by hydroxyl radicals produced by the reaction of the $Co^{II}$ complex with $H_2O_2$.

EXAMPLE 2

A 26-mer 5'-GCAGACTGAGCCTGGGAGCTCTCTGC-3' (SEQ ID No.4) (D, FIG. 1) was used as the DNA substrate. It was prepared according to the same procedures as described in Example 1. Note that substrate D only differs from substrate A in that its bulge contains one less base.

$Co^{II}$(HAPP) $(TFA)_2$ (0.6 $\mu$M) was added to substrate D under the same cleavage reaction conditions as described in Example 1 above. Enhanced and specific cleavage activity was observed at $T_7$ (in the bulge region). The cleavage was found to be inhibited by Pt(terpy)(HET)$^+$.

EXAMPLE 3

$Co^{II}$(HAPP)(TFA)$_2$ (0.6 $\mu$M) was allowed to react under identical conditions as described above with a single-stranded 16-mer of the sequence 5'-GCCAGATCTGAGCCTG-3' (SEQ ID No. 2) (B, FIG. 1) in the presence of $H_2O_2$. No specific cleavage was observed at the 5'-TCT-3' site, even when the concentration of the cobalt complex was increased by 20-fold. The single-stranded substrate was then allowed to anneal with a complementary DNA strand 5'-CAGGGCTCTCTGCC-3' (SEQ ID No. 3) to form a double-stranded DNA with a three-base bulge (C, FIG. 1). When the $Co^{II}$ complex was added to the double-stranded substrate, enhanced DNA cleavage was observed at the 5'-TCT-3' bulge. These results indicate that the $Co^{II}$ complex serves as a DNA bulge-specific cleavage reagent without significant specificity towards the corresponding sequence in the single-stranded DNA.

OTHER EMBODIMENTS

From the above description, one skilled in the art can easily ascertain the essential characteristics of the present invention, and without departing from the spirit and scope thereof, can make various changes and modifications of the invention to adapt it to various usages and conditions. For example, a metal complex of formula (I) can be used to effect cleavage at a nucleic acid substrate with a hairpin loop of 1-5 bases. Thus, other embodiments are also within the claims.

What is claimed is:

1. A metal complex of the following formula:

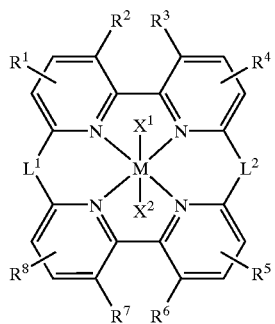

wherein each of $R^1, R^2, R^3, R^4, R^5, R^6, R^7$, and $R^8$, independently, is hydrogen, alkyl, alkoxy, hydroxyl, hydroxylalkyl, halo, haloalkyl, amino, aminoalkyl, alkylcarbonylamino, alkylaminocarbonyl, alkylcarbonyl, alkylcarbonylalkyl, alkoxycarbonyl, alkylcarbonyloxy, cycloalkyl, heterocycloalkyl, aryl, aralkyl, heteroaryl, or heteroaralkyl; each of $R^2$ and $R^3$, and $R^6$ and $R^7$, independently, optionally joining together to form a cyclic moiety fused with the two pyridyl rings to which $R^2$ and $R^3$, or $R^6$ and $R^7$ are bonded; the cyclic moiety, if present, optionally being substituted with alkyl, alkoxy, hydroxyl, hydroxylalkyl, halo, haloalkyl, amino, aminoalkyl, alkylcarbonylamino, alkylaminocarbonyl, alkylcarbonyl, alkylcarbonylalkyl, alkoxycarbonyl, alkylcarbonyloxy, cycloalkyl, heterocycloalkyl, aryl, aralkyl, heteroaryl, or heteroaralkyl;

each of $L^1$ and $L^2$, independently, is —C($R^a$)($R^b$)—, —O—, —S—, or —N($R^c$)—; each of $R^a$, $R^b$, and $R^c$, independently, is hydrogen, alkyl, cycloalkyl, heterocycloalkyl, aryl, heteroaryl, aralkyl, or heteroaralkyl;

M is a Co, Ni, Ru, Rh, Mn, Os, Ag, Cr, Zn, Cd, Hg, Re, Ir, Pt, or Pd ion; and each of $X^1$ and $X^2$, independently, is a labile ligand; or a salt thereof.

2. The metal complex of claim 1, wherein each of $R^1, R^2, R^3, R^4, R^5, R^6, R^7$, and $R^8$, independently, is hydrogen, alkyl, or alkoxy.

3. The metal complex of claim 1, wherein each of $R^2$ and $R^3$, and $R^6$ and $R^7$, independently, join together to form a cyclic moiety; the cyclic moiety being benzene.

4. The metal complex of claim 3, wherein the cyclic moiety is unsubstituted.

5. The metal complex of claim 4, wherein each of $R^1, R^4, R^5$, and $R^8$, independently, is hydrogen, alkyl, or alkoxy.

6. The metal complex of claim 5, wherein each of $R^1, R^4, R^5$, and $R^8$, independently, is hydrogen.

7. The metal complex of claim 6, wherein each of $L^1$ and $L^2$, independently, is —N($R^c$)— where $R^C$ is hydrogen.

8. The metal complex of claim 7, wherein M is Co.

9. The metal complex of claim 8, wherein $X^1$ and $X^2$, independently, is trifluoroacetate.

10. The metal complex of claim 9, wherein said complex is cobalt(II) (hexaazacyclophane) (trifluoroacetate).

11. The metal complex of claim 1, wherein each of $L^1$ and $L^2$, independently, is —S— or —N($R^c$)—.

12. The metal complex of claim 11, wherein each of $L^1$ and $L^2$, independently, is —N($R^c$)— where RC is hydrogen.

13. The metal complex of claim 1, wherein M is Co, Ru, or Mn.

14. The metal complex of claim 13, wherein M is Co.

15. The metal complex of claim 1, wherein $X^1$ and $X^2$, independently, is $H_2O$, Cl, trifluoroacetate, or pyridine.

16. The metal complex of claim 15, wherein $X^1$ and $X^2$, independently, is trifluoroacetate.

* * * * *

SEQUENCE LISTING

```
<160> NUMBER OF SEQ ID NOS: 4

<210> SEQ ID NO 1
<211> LENGTH: 27
<212> TYPE: DNA
<213> ORGANISM: Homo sapiens

<400> SEQUENCE: 1
gcagatctga gcctgggagc tctctgc                                          27

<210> SEQ ID NO 2
<211> LENGTH: 17
<212> TYPE: DNA
<213> ORGANISM: Homo sapiens

<400> SEQUENCE: 2
gccagatctg agccctg                                                     17

<210> SEQ ID NO 3
<211> LENGTH: 14
<212> TYPE: DNA
<213> ORGANISM: Homo sapiens

<400> SEQUENCE: 3
cagggctctc tgcc                                                        14

<210> SEQ ID NO 4
<211> LENGTH: 26
<212> TYPE: DNA
<213> ORGANISM: Homo sapiens

<400> SEQUENCE: 4
gcagactgag cctgggagct ctctgc                                           26
```